(12) United States Patent
Hayashi et al.

(10) Patent No.: US 9,250,296 B2
(45) Date of Patent: *Feb. 2, 2016

(54) TRANSMISSION LINE FOR DIELECTRIC MEASUREMENT AND DIELECTRIC MEASURING DEVICE HAVING THE TRANSMISSION LINE

(71) Applicant: Sony Corporation, Tokyo (JP)

(72) Inventors: Yoshihito Hayashi, Chiba (JP); Shinji Omori, Tokyo (JP); Ikuya Oshige, Kanagawa (JP)

(73) Assignee: Sony Corporation, Tokyo (JP)

( * ) Notice: Subject to any disclaimer, the term of this patent is extended or adjusted under 35 U.S.C. 154(b) by 466 days.

This patent is subject to a terminal disclaimer.

(21) Appl. No.: 13/734,011

(22) Filed: Jan. 4, 2013

(65) Prior Publication Data

US 2013/0120002 A1    May 16, 2013

Related U.S. Application Data

(63) Continuation of application No. 12/283,009, filed on Sep. 9, 2008, now Pat. No. 8,368,410.

(30) Foreign Application Priority Data

Sep. 10, 2007  (JP) ................................. 2007-234702

(51) Int. Cl.
*G01R 27/08* (2006.01)
*G01R 27/26* (2006.01)
*G01R 31/36* (2006.01)
*G01N 27/22* (2006.01)

(52) U.S. Cl.
CPC .............. *G01R 31/36* (2013.01); *G01N 27/221* (2013.01)

(58) Field of Classification Search
CPC ..... G01N 27/221; G01N 27/22; G01N 27/02; G01N 27/06; G01R 31/36; G01R 27/2617; G01R 27/2664
USPC ................................................. 324/663, 693
See application file for complete search history.

(56) References Cited

U.S. PATENT DOCUMENTS

| | | | |
|---|---|---|---|
| 4,734,184 A | 3/1988 | Burleigh et al. |
| 5,772,153 A | 6/1998 | Abaunza et al. |
| 6,338,968 B1 | 1/2002 | Hefti |
| 6,597,185 B1 | 7/2003 | Talanov et al. |
| 6,995,572 B2 | 2/2006 | Arndt et al. |
| 2008/0048678 A1 | 2/2008 | Kurosaka et al. |
| 2008/0238571 A1 | 10/2008 | Kurosaka |

FOREIGN PATENT DOCUMENTS

| | | |
|---|---|---|
| JP | 2002-0286632 A | 10/2002 |
| JP | 2003-509692 A | 3/2003 |

*Primary Examiner* — Amy He
(74) *Attorney, Agent, or Firm* — Wolf, Greenfield & Sacks, P.C.

(57) ABSTRACT

A transmission line substrate includes at least an insulating layer of a predetermined thickness, a pair of conductor layers arranged in a state of being opposed to each other such that the insulating layer is interposed between the conductor layers, the pair of conductor layers functioning as a high-frequency transmission line, and a fault part formed so as to make the conductor layer on one side disconnected, into which a sample to be measured can be introduced.

13 Claims, 6 Drawing Sheets

TRANSMISSION LINE FOR DIELECTRIC MEASUREMENT AND DIELECTRIC MEASURING DEVICE HAVING THE TRANSMISSION LINE

CROSS REFERENCES TO RELATED APPLICATIONS

This application is a continuation of U.S. patent application Ser. No. 12/283,009, entitled "TRANSMISSION LINE FOR DIELECTRIC MEASUREMENT AND DIELECTRIC MEASURING DEVICE HAVING THE TRANSMISSION LINE," filed Sep. 9, 2008, which claims the benefit under 35 U.S.C. §119 of Japanese Patent Application JP 2007-234702 filed with the Japan Patent Office on Sep. 10, 2007. The contents of these applications are hereby incorporated by reference in their entireties.

BACKGROUND OF THE INVENTION

1. Field of the Invention

The present invention relates to a technique for obtaining information on an electrical characteristic of a sample to be measured, and particularly to a novel technique for measuring the permittivity of a sample at a minute fault part formed in a conductor layer part of a transmission line having a predetermined structure.

2. Description of the Related Art

There are various measuring techniques for determining the properties (for example a chemical structure and an internal structure) of a substance. For example, the permittivity (dielectric permittivity) of a substance can be an important property value in determining the properties (for example a chemical structure and an internal structure) of the substance. A dielectric measurement method is carried out in a frequency domain using an impedance analyzer or a network analyzer. There is also a method of converting data measured in a time domain using time domain reflectometry (TDR method) into a frequency domain by Fourier analysis or the like. Recently, attenuated total reflection spectroscopy (ATR method) has been proposed as a permittivity measuring method. Japanese Patent Laid-Open No. 2002-286632 discloses an example of the technique.

In related art, methods widely and generally used when the permittivity (dielectric spectrum) of a sample is to be measured include for example methods in which the target sample is measured in a state of being interposed between two electrodes in the form of a capacitor, the sample is measured after being injected into a space including an electrode in a cylindrical shape or a coaxial shape, and measurement is performed with a termination type electrode soaked in a container containing the sample.

Sample quantities necessary in such existing permittivity measuring methods are 100 µL or more, excluding a case of a macromolecule that can form a thin film, for example. Therefore, such existing permittivity measuring methods are fundamentally unsuitable for measurement of a precious sample. In a case of measuring a liquid sample using an electrode in a coaxial shape, a sample in a quantity of about 40 µL can be measured. However, this electrode is unsuitable for measurement of a sample other than a liquid (for example a sample in the form of a gel). In addition, any of the above-described existing methods requires skills to prevent the mixing in of air bubbles when injecting a sample, and thus has a limited potential for development into automatic measurement techniques.

In addition, with ideas as an extension of the existing permittivity measuring methods, it is difficult to realize a compact measuring device because there are limitations to the size and shape of the electrode itself and the like.

SUMMARY OF THE INVENTION

The present invention is suitable for techniques of measuring an electrical characteristic of a precious sample in a very small quantity. It is desirable to provide a technique that can provide an inexpensive and compact measuring device.

According to an embodiment of the present invention, there is first provided a transmission line substrate including at least an insulating layer (dielectric layer) of a predetermined thickness, a pair of conductor layers arranged in a state of being opposed to each other such that the insulating layer is interposed between the conductor layers, the pair of conductor layers functioning as a high-frequency transmission line, and a fault part formed so as to make the conductor layer on one side of the pair of conductor layers disconnected, into which a sample to be measured can be introduced. Incidentally, this transmission line substrate may be said to belong to the category of a concept referred to generally as a strip line, but is different because a typical existing strip line does not have a structure equivalent to the fault part.

A method of introducing the sample into the fault part is not particularly limited. For example, the sample may be dropped from above. Alternatively, a flow path for sample introduction may be provided which flow path is formed such that the fault part is a part of the flow path, and the sample may be sent as a solution from the flow path to the fault part, for example.

Next, the present embodiment provides a multiple transmission line substrate having a plurality of high-frequency transmission lines as described above arranged in parallel with each other. Further, a flow path for sample introduction may be formed so as to pass a plurality of fault parts in the multiple transmission line substrate. In this case, the sample is sent as a solution inside the flow path 9, and the sample passes one fault part after another. Therefore the multiple transmission line substrate is very suitable for an application in which the dielectric measurement of the sample is continually performed with a time lag.

In addition, according to an embodiment of the present invention, there is provided an electrical measuring device for obtaining information on an electrical characteristic of a sample to be measured using the above-described transmission line substrate, the electrical measuring device including a power supply section for supplying power to the conductor layers forming the transmission line substrate, a sample introducing section for introducing the sample into the fault part directly or via a flow path, and a measuring section for measuring impedance that can be changed by introducing the sample into the fault part. There is also provided an electrical measuring device further including an analyzing section for obtaining permittivity of the sample on a basis of the impedance.

According to an embodiment of the present invention, a sample is introduced into a minute fault part provided in one side of a plurality of conductor layers forming a transmission line substrate to analyze the impedance of the sample and in turn an electrical characteristic such as permittivity or the like of the sample on the basis of change in the impedance. Therefore, the quantity of a sample which quantity is required for measurement may be very small, and the electrical characteristic of the sample can be measured efficiently. In addition, the transmission line substrate has a very simple configuration, and requires low material cost and low manufacturing cost. It is thus possible to provide an electrical measuring device such as a dielectric measuring device or the like that is compact and inexpensive.

DETAILED DESCRIPTION OF THE PREFERRED EMBODIMENTS

An example of preferred embodiments of a transmission line substrate and a dielectric measuring device using the transmission line substrate according to an embodiment of the present invention will hereinafter be described with reference to the accompanying drawings.

Figure 1:
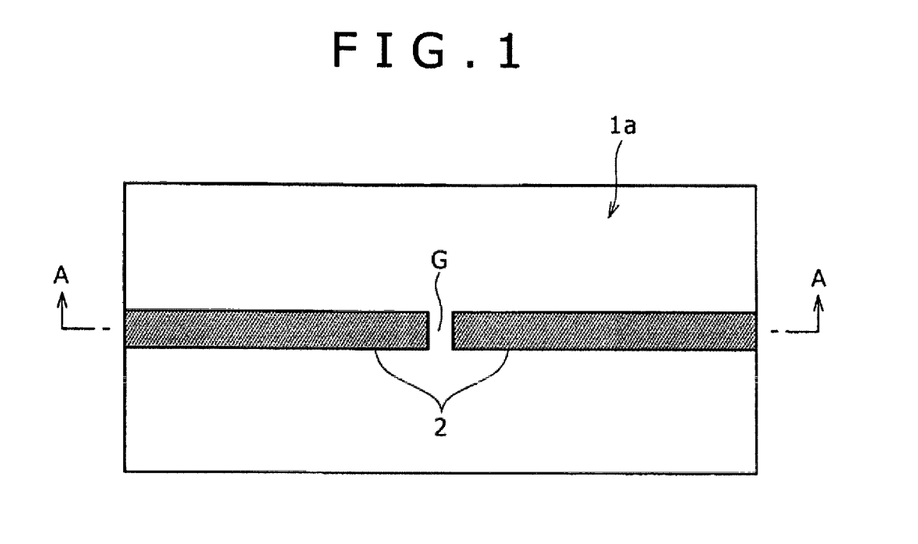
FIG. 1 is a plan view of a substrate of a simplest configuration provided with a transmission line (strip line) (hereinafter referred to as a transmission line substrate) according to an embodiment of the present invention as viewed from above.
Figure 2:
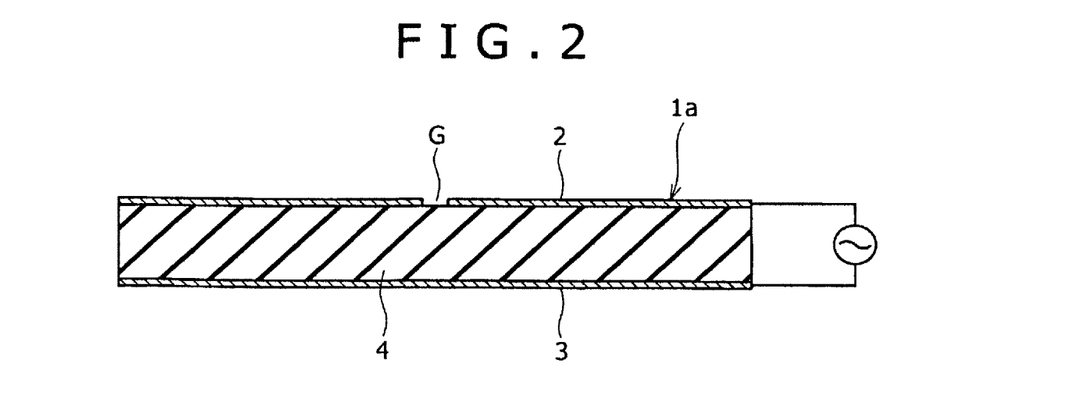
FIG. 2 is a vertical sectional view taken along the arrow line A-A of FIG. 1.

FIG. 1 is a plan view of a substrate of a simplest configuration provided with a transmission line (strip line) (hereinafter referred to as a transmission line substrate) as viewed from above. FIG. 2 is a vertical sectional view taken along the arrow line A-A of FIG. 1.

A conductor layer 2 serving as a high-frequency transmission line is formed in an exposed state on the upper surface of the transmission line substrate 1a. In addition, a small fault part (gap) G is formed at a predetermined position (for example an intermediate position) of the conductor layer 2, so that the conductor layer 2 is in a disconnected state (see FIG. 1). At the part of the fault part G in contact with a sample, platinum black plating or the like can be performed to thereby increase electrode surface area and reduce electrode polarization. Incidentally, the transmission line substrate 1a is formed by an insulating material (the material is not particularly limited, and an example of the material is alumina).

Next referring to the vertical sectional view (FIG. 2) of the transmission line substrate 1a, a conductor layer 3 is provided (normally grounded) as a lowermost layer of the substrate 1a. The conductor layer 3 is opposed to the conductor layer 2 with an insulating layer 4 of a predetermined thickness (about 0.5 mm, for example) interposed between the conductor layer 3 and the conductor layer 2. That is, the transmission line substrate 1a has a sandwich structure in which the insulating layer 4 is sandwiched in between the conductor layers 2 and 3. Incidentally, each of the conductor layers 2 and 3 can for example be printed onto the surface (the upper surface or the lower surface) of the insulating layer 4 by evaporation or the like.

The width of the conductor layers 2 and 3 is determined according to a purpose or a use. For example, the width of the conductor layer 2 is designed to be about 0.5 mm, and the width of the conductor layer 3 is designed to be about 20 mm over the entire bottom surface of the substrate. The thickness of the conductor layers 2 and 3 is also determined according to a purpose or a use. For example, the thickness of the conductor layers 2 and 3 is designed to be a few μm.

The characteristic impedance of the transmission line (strip line) of such a configuration is determined by the permittivity of the insulating layer 4, the thickness of the insulating layer 4, the width of the conductor layer 2 on the upper surface, and the like. Generally, 50 ohms (Ω) is selected. With the configuration of such a transmission line (strip line), an electric signal can typically be transmitted in a quasi-TEM mode.

A feature of the transmission line (strip line) according to an embodiment of the present invention is that a small fault part (gap) G is formed at a selected predetermined position of the conductor layer 2 on the upper side, so that the conductor layer 2 is in a disconnected state. When a sample to be measured is introduced into such a fault part G by a selected method, an electrical characteristic such as permittivity or the like of the sample can be obtained by applying a certain analysis to a signal obtained as a result of transmitting an electric signal to the conductor layers 2 and 3.

The configuration having the fault part G opening upward has another advantage of enabling an electrical characteristic of even a sample of high viscosity (for example a sample in the form of a gel) to be measured by for example dropping (spotting), injecting, or filling the sample into the fault part G. This fault part G is formed as a small region, and thus has a fundamental advantage of requiring only a very small sample quantity for measurement. For example, when the gap length of the fault part G (the length of the gap) is designed to be about 10 μm, a sample quantity of a few ten to a few hundred nanoliters is a sufficient quantity to be secured for measurement. As a method for introducing a sample into the fault part G, a flow path passing through the fault part G may be provided.

Figure 3:
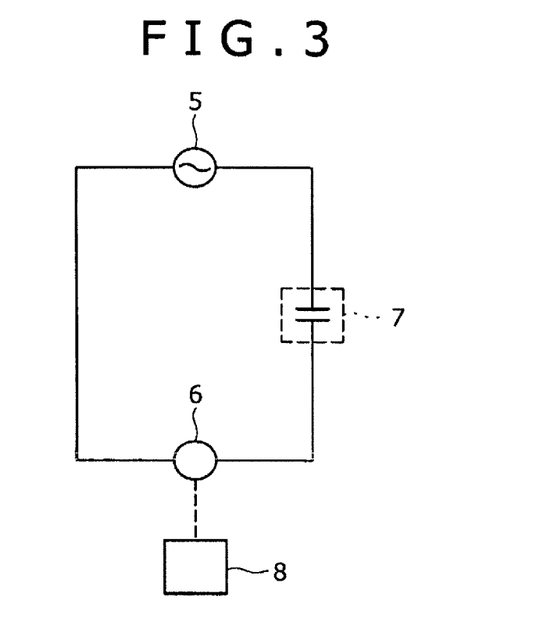
FIG. 3 is a diagram showing a fundamental configuration common to embodiments of an electrical measuring device according to the present invention.

FIG. 3 is a diagram showing a fundamental configuration common to embodiments of an electrical measuring device according to an embodiment of the present invention. Reference numeral 5 in FIG. 3 denotes a high-frequency alternating-current power supply (electric signal transmitter) or a step pulse transmitter (a transmitter for time domain reflectometry (TDR) measurement can also be used). Reference numeral 6 denotes a measuring unit (receiver) for measuring a change in impedance obtained by a measuring section 7 having a transmission line. Reference numeral 8 denotes an analyzing unit for analyzing an electric signal (signal) from the measuring unit 6 to obtain electrical information such as permittivity or the like of a sample to be measured.

Figure 4:
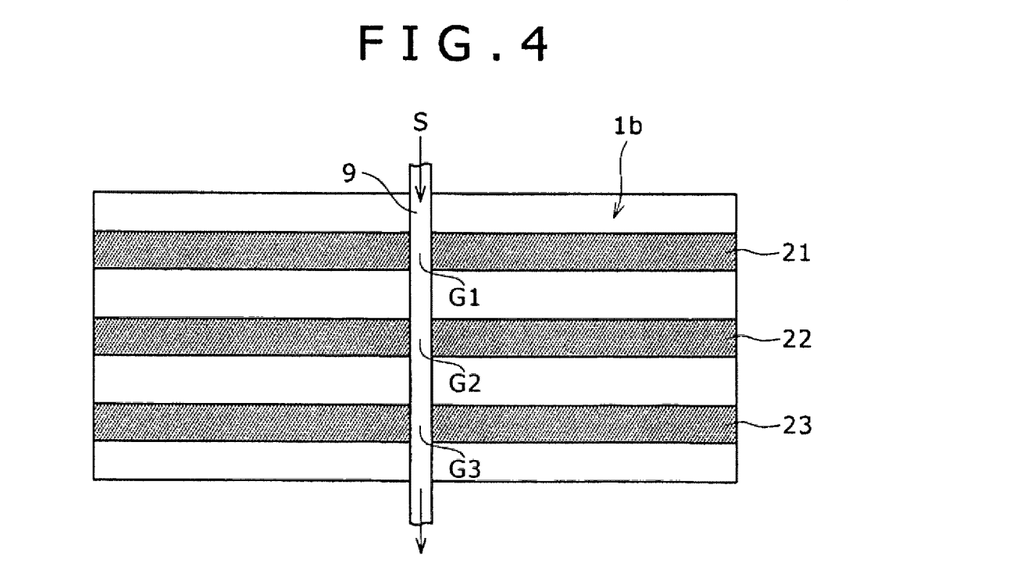
FIG. 4 is a plan view when an example of modification (reference 1b) of the transmission line substrate 1a is viewed from above.

FIG. 4 is a plan view when an example of modification (reference 1b) of the transmission line substrate 1a is viewed from above. A plurality of pairs of an upper conductor layer and a lower conductor layer each are arranged in parallel with each other on the substrate 1b, whereby multiple transmission lines are formed. Incidentally, the lower conductor layers (not shown in FIG. 4) may be provided as a conductor layer common to the entire bottom surface of the substrate 1b.

FIG. 4 shows three conductor layers 21, 22, and 23 printed on the upper surface of the multiple transmission line substrate 1b. Small fault parts G1, G2, and G3 are provided to the conductor layers 21, 22, and 23, respectively. Further, a flow path 9 formed so as to pass through all of these fault parts G1, G2, and G3 is extended.

In this case, the flow path 9 enables a sample S to be measured to be introduced to the fault parts G1, G2, and G3 in order in time series by physical means selected appropriately such as pressurization, negative pressure suction, capillarity or the like (see FIG. 4). In the configuration of such a multiple transmission line substrate, when the sample passes through the flow path 9, the sample passes the fault parts G1, G2, and G3 in order. Therefore the configuration of the multiple transmission line substrate is very suitable for an application in which an electrical characteristic of a sample is continually measured (for example monitored) at time intervals.

For example, in a case where a property (shape, structure or the like) of a substance changes with the passage of time, a case where chemical reaction or interaction progresses according to time change, a measuring system for determining the presence or absence and an amount of the change in the property of the substance and the chemical reaction or the interaction can be constructed. When the flow path 9 is used, it is also possible to wash the flow path 9 and the fault parts G1 to G3 automatically.

Incidentally, an electric signal for measurement can be transmitted to the plurality of conductor layers 21, 22, and 23 in order by using switching means synchronized with measurement timing.

Figure 5:
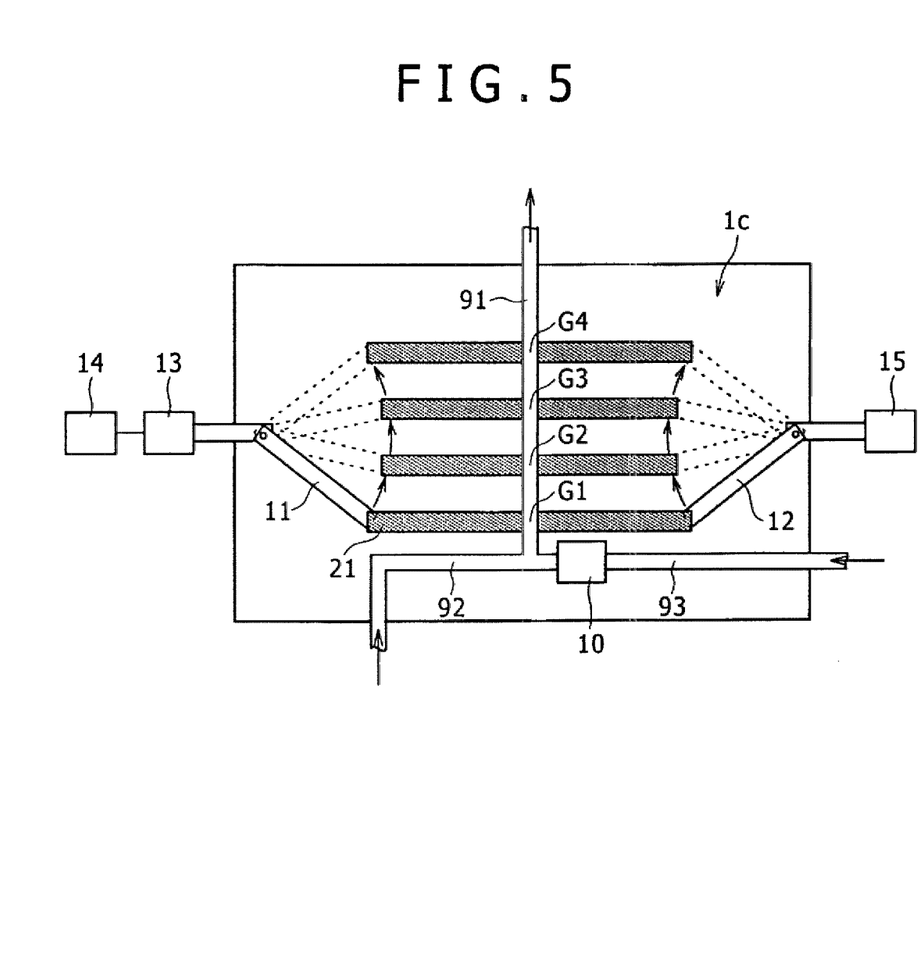
FIG. 5 is a diagram (a plan view as viewed from above) showing a principal configuration of a substrate provided with multiple transmission lines and an embodiment of switching means.

FIG. 5 is a diagram (a plan view as viewed from above) showing a principal configuration of a multiple transmission line substrate provided with an embodiment of the above-described switching means.

A total of four conductor layers 21, 22, 23, and 24 are arranged in parallel with each other at regular intervals on the multiple transmission line substrate 1c. In addition, fault parts G1 to G4 are provided at one position of the respective conductor layers 21 to 24. In addition, a flow path 91 formed so as to pass all of the fault parts G1, G2, G3, and G4 is provided. Further, a flow path 92 communicating with the flow path 91 and a flow path 93 formed so as to be opened and closed by a valve 10 are provided in an extended manner.

The flow path 92 and the flow path 93 are provided in the present embodiment in order to allow different samples or the like to be introduced from different routes. For example, a substance to be measured can be introduced from one (for example the flow path 92), and a medicinal agent that can chemically change the substance can be introduced from the other (for example the flow path 93). Alternatively, a substance to be measured can be introduced from one (for example the flow path 92), and a substance that can interact with the substance to be measured (including hybridization) can be introduced from the other (for example the flow path 93).

Reference numerals 11 and 12 in FIG. 5 denote a conductor for switching. These conductors for switching can select the conductors 22 to 24 for transmitting an electric signal for measurement automatically in predetermined timing by intermittent motion (see thick arrows in FIG. 5). Thus, electric signals reflecting an electrical characteristic of a sample introduced into the fault parts G1, G2, G3, and G4 can be obtained sequentially.

Incidentally, reference numeral 13 in FIG. 5 denotes a power supply (transmitter). Reference numeral 14 denotes a receiver for measuring an input wave and a reflected wave. Reference numeral 15 denotes a receiver for measuring a transmitted wave. In this case, the "input wave" is an electric signal transmitted at a certain frequency from the transmitter in frequency domain measurement, and a sinusoidal voltage, for example, is used as input wave. Incidentally, frequency dependence of an electrical property such as permittivity or the like of a sample can be obtained by sequentially changing input frequency and performing measurement (spectral measurement). In time domain measurement, the input wave is a step voltage or a pulse voltage repeatedly transmitted at regular intervals from a step pulse transmitter. In the case of time domain measurement, frequency dependence of an electrical property such as permittivity or the like of a sample, which is equivalent to that of frequency domain measurement, can be obtained by data analysis including Fourier analysis. The "reflected wave" in both frequency domain measurement and time domain measurement is an electric signal obtained as a result of the input wave sequentially propagating through the conductor 11 for switching and the conductor 21, 22, 23, or 24 and reaching the gap part, and a part of the electric signal that has reached the gap part being reflected and then returned on a reverse route. When a sample is present in the gap part, the reflected wave includes information on an electrical property such as permittivity or the like of the sample. The "transmitted wave" is an electric signal observed when a part of the electric signal that has sequentially propagated through the conductor 11 for switching and the conductor 21, 22, 23, or 24 and reached the gap part is transmitted because of presence of the sample in the gap part and then passed through the transmission line on the opposite side from the side of the transmitter. This transmitted wave also includes information on an electrical property such as permittivity or the like of the sample.

In a transmission line substrate used in an experiment, alumina having a thickness of 0.635 mm is used as an insulating layer forming a transmission line, a conductor layer is formed of gold, the conductor layer is designed to have a width of 0.64 mm and a thickness of 2.5 µm, and the interval width of a fault part is designed to be 500 µm. Both ends of the substrate are connected to a measuring device by a coaxial cable via probe contact. This measuring device is formed by setting a TDR module (54754A manufactured by Agilent) including a pulse generator and a sampling head to a digital oscilloscope 86100C manufactured by Agilent, which oscilloscope is capable of two-channel time domain measurement. A step pulse having a voltage of 200 mV and a rising time of about 40 picoseconds was made to enter one end of the substrate from the measuring device, and measurement of a wave reflected at the fault part of the conductor layer (S11 measurement) and observation of a waveform transmitted by the fault part (S21 measurement) were performed.

In this experiment, an air was measured first. Then, 5 µL of each of (1) water, (2) rabbit preserved blood, and (3) a saline solution adjusted to have a same electric conductivity as the rabbit preserved blood was dropped into the fault part as a sample in a liquid form. Incidentally, transmission measurement (S21 measurement) was performed using a transmission line substrate without a fault part formed therein (that is, the transmission line substrate has a same transmission line as an ordinary transmission line that is not disconnected) for a purpose of obtaining basic data to be used for analysis.

Figure 6:
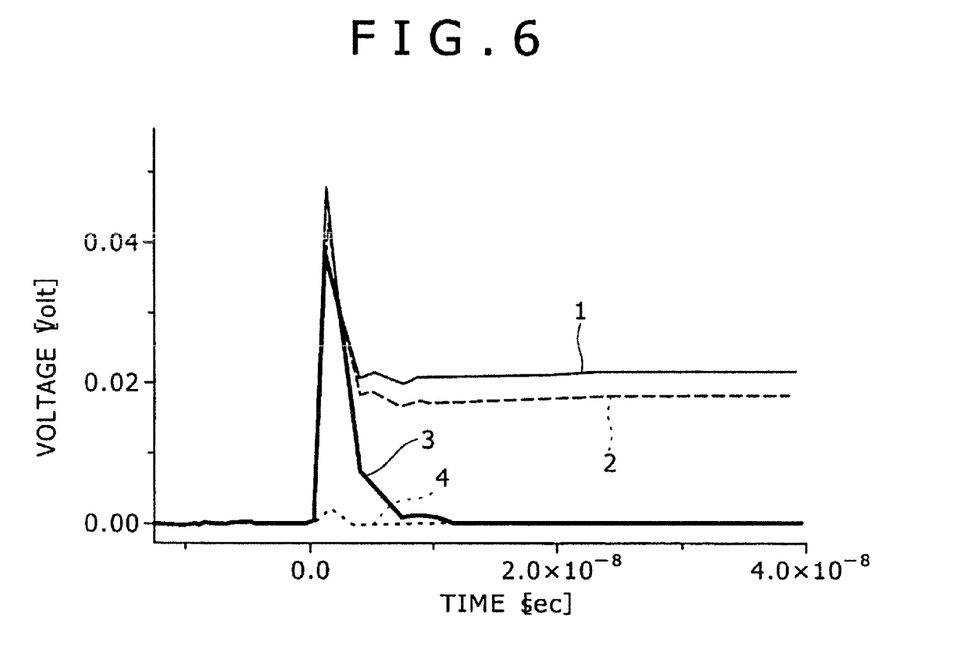
FIG. 6 is a graph (drawing substitute graph) showing S21 measurement data obtained in an experiment in a magnified state for a short time range.

FIG. 6 is a graph (drawing substitute graph) showing S21 measurement data obtained in the experiment in a magnified state for a short time range. As is clear from the graph, measurement results are clearly different for the different samples. This difference reflects difference in permittivity and conductivity between the samples. Incidentally, in FIG. 6 (graph), a graph line 1 represents data obtained by S21 measurement of a rabbit erythrocyte suspension, a graph line 2 represents data obtained by S21 measurement of a saline solution, a graph line 3 represents data obtained by S21 measurement of pure water, and a graph line 4 represents data obtained by S21 measurement of an air.

Figure 7:
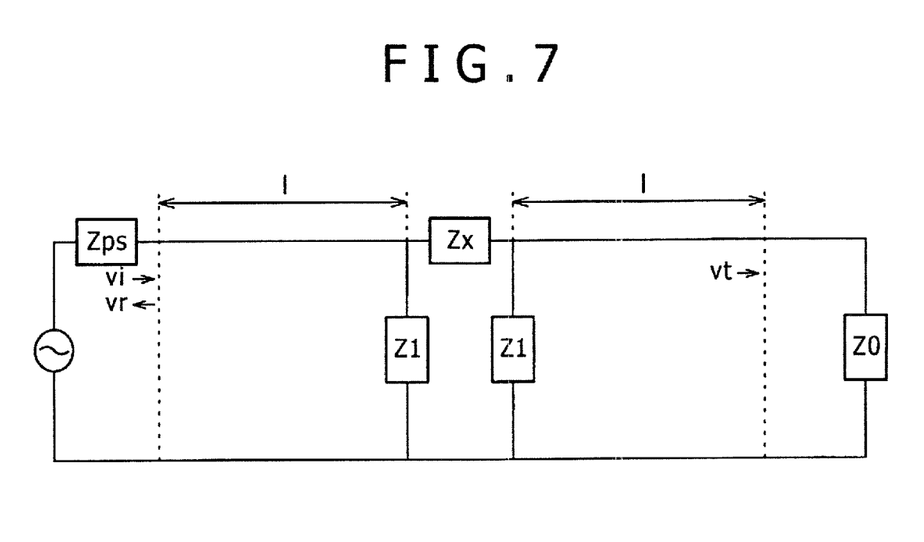
FIG. 7 is a diagram showing an equivalent circuit related to measurement with a transmission line substrate used in the experiment.

An embodiment of a measurement data analyzing method will next be described. This analyzing method can be used in an analyzing unit forming a measuring device according to an embodiment of the present invention. FIG. 7 is a diagram showing an equivalent circuit related to measurements with the substrate used in the present experiment. The complex permittivity $\in^*$ to be obtained of a sample is related to complex impedance ZX in a relation of the following equation. Incidentally, j is an imaginary unit, $\omega$ is angular frequency, and C1 is a capacitance value related to the measurement sensitivity of the substrate.

$$Z_x = (j\omega \in^* C_1)^{-1} \quad \text{[Equation 1]}$$

On the other hand, a waveform Vr reflected by the fault part formed in the transmission line and a waveform Vt transmitted by the fault part are affected by the complex impedance $Z_x$. Thus, the complex permittivity $\in^*$ can be obtained by analyzing these waveforms. Concrete methods for obtaining the complex permittivity $\in^*$ include (A) a direct method, (B) a reflection-transmission combination method, (C) a reference method, and the like.

(A) Direct Method

The complex permittivity $\in^*$ can be obtained by one of the following equations using an incident waveform Vi and the transmitted waveform Vt or the reflected waveform Vr.

$$\varepsilon^* = \frac{j}{2\omega Z_0 C_1} \frac{(1 + z_1^{-1})^2}{1 + z_1^{-1} - \bar{v}_i / \bar{v}_t} \quad \text{[Equation 2]}$$

where $\bar{v}_i$ and $\bar{v}_t$ are waveforms in a frequency domain, and can be obtained by subjecting Vi and Vt as time domain waveforms to a Laplace transform (the same is true in the following).

$$\varepsilon^* = \frac{j}{2\omega Z_0 C_1}(1 + z_1^{-1})\left(1 - \frac{\bar{v}_i / \bar{v}_r}{1 + z_1^{-1} + z_1^{-1}\bar{v}_i / \bar{v}_r}\right) \quad \text{[Equation 3]}$$

$Z_0$ in the equation is the characteristic impedance of the transmission line, and 50$\Omega$ is generally selected as $Z_0$. In this case, Equation 2 and Equation 3 above can be simplified into Equation 4 and Equation 5, respectively, by setting $Z_1$ infinite.

$$\varepsilon^* = \frac{j}{2\omega Z_0 C_1} \frac{1}{1 - \bar{v}_i / \bar{v}_t} \quad (z_1 \to \infty) \quad \text{[Equation 4]}$$

$$\varepsilon^* = \frac{j}{2\omega Z_0 C_1}(1 - \bar{v}_i / \bar{v}_r) \quad (z_1 \to \infty) \quad \text{[Equation 5]}$$

(B) Reflection-Transmission Combination Method

The complex permittivity $\in^*$ can be obtained by the following equation using both the transmitted waveform Vt and the reflected waveform Vr.

$$\varepsilon^* = \frac{1}{j\omega Z_0 C_1} \frac{2\bar{v}_i \bar{v}_t}{(\bar{v}_i + \bar{v}_r - \bar{v}_t)(\bar{v}_i + \bar{v}_r + \bar{v}_t)} \quad \text{[Equation 6]}$$

At this time, $Z_1$ can be obtained by the following equation.

$$z_1 = \frac{\bar{v}_i + \bar{v}_r + \bar{v}_t}{\bar{v}_i - \bar{v}_r - \bar{v}_t} \quad \text{[Equation 7]}$$

(C) Reference Method

The complex permittivity $\in^*$ of a sample can be obtained with higher accuracy by measuring a reference sample (standard sample) whose complex permittivity is already known in addition to the sample in order to obtain the complex permittivity $\in^*$ of the sample. Letting $\in^*r$ be the complex permittivity of the reference, and letting Vrr and Vrt be a reflected wave and a transmitted wave, respectively, in the reference measurement, the complex permittivity $\in^*$ of the sample can be obtained by one of the following equations.

$$\varepsilon^* = \varepsilon_r^* \frac{\lambda_t}{1 + j2\omega Z_0 C_1 (1 - \lambda_t)(1 + z_1^{-1})^{-1} \varepsilon_r^*} \quad \text{[Equation 8]}$$

$(\lambda_t = \bar{v}_i / \bar{v}_{ri})$ $$\varepsilon^* = \frac{1}{j2\omega Z_0 C_1}(1 + z_1^{-1})\frac{\substack{(1 + z_1^{-1})(1 - z_1^{-1})(1 - \lambda_r) + \\ j2\omega Z_0 C_1 (1 - z_1^{-1}(1 - \lambda_r))\varepsilon_r^*}}{\substack{(1 + z_1^{-1})((1 - z_1^{-1})\lambda_r + z_1^{-1}) + \\ j2\omega Z_0 C_1 z_1^{-1}(1 - \lambda_r)\varepsilon_r^*}} \quad \text{[Equation 9]}$$

$(\lambda_r = \bar{v}_r / \bar{v}_{rr})$

In this case, by setting $Z_1$ infinite, Equation 8 and Equation 9 shown above can be simplified into the following Equation 10 and Equation 11, respectively. Further, the following Equation 12 can be derived by considering both Equation 8 and Equation 9 shown above.

$$\varepsilon^* = \varepsilon_r^* \frac{\lambda_t}{1 + j2\omega Z_0 C_1 (1 - \lambda_t) \varepsilon_r^*} \quad \text{[Equation 10]}$$

$(z_1 \to \infty)$ $$\varepsilon^* = \varepsilon_r^* \frac{j}{2\omega Z_0 C_1}[1 - (1 + j2\omega Z_0 C_1 \varepsilon_r^*)\lambda_r^{-1}] \quad \text{[Equation 11]}$$

$(z_1 \to \infty)$ $$\varepsilon^* = \varepsilon_r^* \frac{\left| \begin{array}{c} (1 - \lambda_t \lambda_r) + j(1 - \lambda_t)(1 - \lambda_r) \\ \omega Z_0 C_1 \varepsilon_r^* \pm \\ j\sqrt{1 - \omega^2 Z_0^2 C_1^2 \varepsilon_r^{*2} + j2\omega Z_0 C_1 \varepsilon_r^* \frac{1 - \lambda_t}{1 - \lambda_r}} \end{array} \right|}{\substack{(1 - \lambda_r) + (1 - \lambda_t)(\lambda_r / \lambda_t) + \\ j2\omega Z_0 C_1 \varepsilon_r^*(1 - \lambda_t)(1 - \lambda_r)}} \quad \text{[Equation 12]}$$

Stray Capacitance Correction

More accurate analysis can be performed when the stray capacitance Cr of the fault part is corrected. When the stray capacitance can be ignored, the relation between the complex permittivity of the sample and the complex impedance is expressed by the above-described Equation 1. However, when the stray capacitance Cr cannot be ignored, effect of the stray capacitance Cr comes into the impedance of the measuring system in the form of the following Equation 13.

$$z_x = \frac{1}{j\omega(C_1 + C_r)Z_0} \quad \text{[Equation 13]}$$

In this case, using two reference samples whose complex permittivity is already known, $C_1$ from which the effect of the stray capacitance Cr is eliminated can be obtained by the following Equation 14 or Equation 15.

$$C_1 = \frac{1}{2\omega Z_0} \frac{(\bar{v}_{r1t} - \bar{v}_{r2t})\bar{v}_i}{j(\varepsilon_{r1}^* - \varepsilon_{r2}^*)(\bar{v}_i - \bar{v}_{r1t})(\bar{v}_i - \bar{v}_{r2t})} \quad \text{[Equation 14]}$$

$$C_1 = \frac{j}{2\omega Z_0} \frac{(\bar{v}_{r1r} - \bar{v}_{r2r})\bar{v}_i}{(\varepsilon_{r1}^* - \varepsilon_{r2}^*)\bar{v}_{r1r}\bar{v}_{r2r}} \quad \text{[Equation 15]}$$

Once $C_1$ (capacitance value related to measurement sensitivity) is determined by Equation 14 or Equation 15 shown above, measurement can be performed with one of the two reference samples in Equation 14 or Equation 15 as an unknown sample to obtain the complex permittivity $\in^*$ of the target sample.

An experiment was actually conducted to evaluate $C_1$ and Cr and verify fault part interval dependence and sample quantity dependence.

First, four kinds of samples having different fault part intervals were prepared as substrate provided with a transmission line (see FIG. 1), and pure water and glycerol whose complex permittivity was already known were measured. From the measurement data, $C_1$ was obtained by Equation 14. The result is shown in the next "Table 1." This result indicates that the value of $C_1$ is changed by varying the interval length of the fault part, that is, measurement sensitivity can be changed by varying the interval length of the fault part.

TABLE 1

Value of $C_1$ Obtained by Equation 14 (Unit: fF)

| Fault Part Interval Length | Quantity of Sample Solution Dropped into Fault Part | | | | | | |
|---|---|---|---|---|---|---|---|
| | 5 μl | 10 μl | 15 μl | 20 μl | 50 μl | 100 μl | 200 μl |
| 30 μm | 12.46 | 13.36 | 13.84 | 14.31 | 15.12 | 15.28 | 15.33 |
| 100 μm | 9.80 | 10.76 | 11.33 | 11.40 | 11.86 | 12.40 | 12.56 |
| 500 μm | 6.58 | 7.61 | 7.88 | 8.42 | 9.50 | 9.87 | 10.21 |
| 1000 μm | 4.17 | 5.03 | 5.79 | 5.93 | 7.13 | 7.18 | 7.66 |

On the other hand, considering the presence of the stray capacitance Cr, the above-described Equation 6 is rewritten as in the following Equation 16.

$$C_1 \varepsilon^* + C_r = \frac{1}{j\omega Z_0} \frac{2\bar{v}_i \bar{v}_t}{(\bar{v}_i + \bar{v}_r - \bar{v}_t)(\bar{v}_i + \bar{v}_r + \bar{v}_t)} \quad \text{[Equation 16]}$$

By analyzing a result of measurement of pure water using Equation 16, and further considering $C_1$ shown in "Table 1," the stray capacitance Cr was obtained as in the next "Table 2." This result shows that because the stray capacitance Cr is sufficiently lower than $C_1$ (capacitance value related to measurement sensitivity), in the transmission line substrate used in the present experiment, considering measurement errors, no problem is presented even when the stray capacitance Cr is ignored in actual measurement.

TABLE 2

Value of Cr (unit: fF)

| Fault Part Interval Length | Quantity of Sample Solution Dropped into Fault Part | | | | | | |
|---|---|---|---|---|---|---|---|
| | 5 μl | 10 μl | 15 μl | 20 μl | 50 μl | 100 μl | 200 μl |
| 30 μm | 0.58 | 0.57 | 0.45 | 0.55 | 0.56 | 0.54 | 0.06 |
| 100 μm | 0.37 | 0.30 | 0.25 | 0.22 | 0.27 | 0.31 | 0.29 |
| 500 μm | 0.09 | 0.03 | −0.06 | 0.01 | 0.01 | −0.02 | −0.01 |
| 1000 μm | 0.00 | −0.02 | −0.07 | −0.05 | −0.06 | −0.09 | −0.10 |

Figure 8:
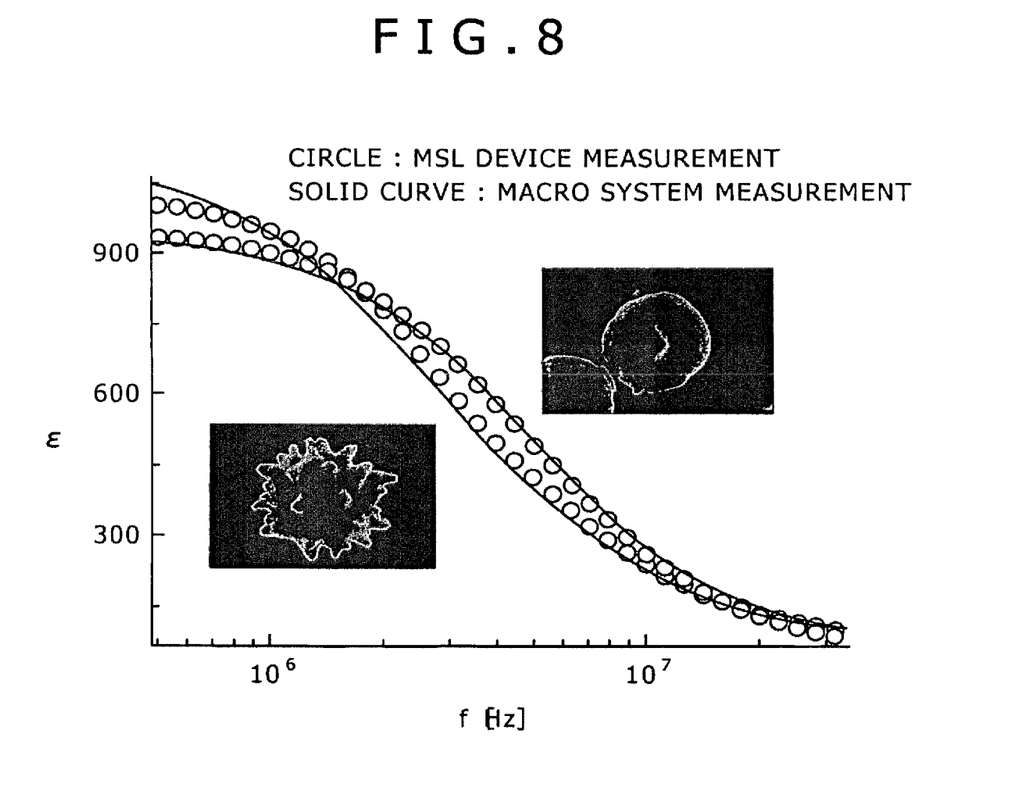
FIG. 8 is a graph showing a result obtained by measuring an erythrocyte suspension and a saline solution having a same electric conductivity as the erythrocyte suspension using the transmission line substrate according to the above-mentioned embodiment of the present invention (see FIG. 1), and analyzing the measurement data.

Next, an actual experiment in measurement of an erythrocyte suspension was performed. FIG. 8 shows a result obtained by measuring an erythrocyte suspension and a saline solution having a same electric conductivity as the erythrocyte suspension using the transmission line substrate according to the foregoing embodiment of the present invention (see FIG. 1), and analyzing the measurement data. Incidentally, circles plotted in FIG. 8 are results of measurement by the present experiment, and curves are results of dielectric spectrometry according to an existing method. Incidentally, the dielectric spectrometry according to the existing method was performed as follows. A sample of about 160 μL was injected between two parallel plate type electrodes plated with platinum black (a diameter of 8 mm and a distance of 3.5 mm between the electrodes), and capacitance and conductance were measured at each frequency by an impedance analyzer (4294A model) manufactured by Agilent. Complex permittivity $\in^*$ was obtained by analyzing the measured values by an existing analyzing method (for example a document "Asami et al., Biochim. Biophys. Acta Journal, Vol. 778, pp. 559-569 (1984)").

Two kinds of erythrocytes of adjusted shape were prepared. Analysis was performed on the basis of the above-described Equation 14. In this case, the value of C1 was obtained from the data in "Table 1" shown above. As described above, Equation 14 is an equation for obtaining the value of C1 using two reference samples. In this case, because the value of C1 was already known, one of the two references was replaced with an unknown sample (an erythrocyte suspension in this case), and a saline solution was used as the other reference sample. The complex permittivity of the unknown sample was thereby calculated. The result coincides with the result of measurement by the ordinary dielectric spectrometry. Thus, a measuring system provided by the present embodiment can be a new dielectric spectrometry.

It is generally known that in dielectric measurement of a conductive liquid or gel, an error is increased as the frequency of the measurement is lowered because electrode polarization occurs. Several techniques for reducing effect of the electrode polarization are known in an ordinary dielectric relaxation measuring method. One of the techniques uses a saline solution as a reference. The present experiment has also shown that measurement accuracy is improved by using a saline solution.

The present embodiment can be used as a novel measuring technique for measuring an electrical characteristic, for example permittivity of a sample, especially a precious sample in a very small quantity.

It should be understood by those skilled in the art that various modifications, combinations, sub-combinations and alterations may occur depending on design requirements and other factors insofar as they are within the scope of the appended claims or the equivalents thereof.

What is claimed is:

1. An electrical measuring device for obtaining information on an electrical characteristic of a sample, the electrical measuring device comprising:
   a plurality of high-frequency transmission lines arranged in parallel with each other, each of the high-frequency transmission lines including:
   an insulating layer,
   a first conductor layer disposed adjacent to the insulating layer and having two ends located opposite one another,
   a second conductor layer disposed adjacent to the insulating layer on a side opposite the first conductor layer and having two ends located opposite one another, the two ends of the second conductor layer being electrically connected to one another, and
   a fault part formed in the first conductor layer so as to electrically disconnect the two ends of the first conductor layer unless a sample to be measured is introduced into the fault part.

2. The electrical measuring device according to claim 1, further comprising a flow path for sample introduction which passes a plurality of fault parts.

3. The electrical measuring device according to claim 1, further comprising a flow path for sample introduction having the fault part as a part of the flow path.

4. The electrical measuring device according to claim 1, further comprising:
   a power supply section configured to supply power to the conductor layers forming the plurality of high-frequency transmission lines;
   a sample introducing section configured to introduce the sample into the fault part directly or via a flow path; and
   a measuring section configured to measure impedance that can be changed by introducing the sample into the fault part.

5. The electrical measuring device according to claim 4, further comprising an analyzing section configured to obtain permittivity of the sample based on the measured impedance.

6. The electrical measuring device according to claim 1, further comprising a conductor switch configured to provide an electrical connection sequentially between a transmitter and each of the plurality of high-frequency transmission lines.

7. The electrical measuring device according to claim 1, further comprising a receiver configured to measure an input wave signal to be transmitted through at least one of the high-frequency transmission lines.

8. The electrical measuring device according to claim 7, wherein the receiver is configured to measure a reflected wave signal having been transmitted through a portion of the at least one of the high-frequency transmission lines.

9. An electrical measuring device for obtaining information on an electrical characteristic of a sample, the electrical measuring device comprising:
   a high-frequency transmission line including:
   an insulating layer,
   a first conductor layer disposed adjacent to the insulating layer and having two ends located opposite one another,
   a second conductor layer disposed adjacent to the insulating layer on a side opposite the first conductor layer and having two ends located opposite one another, the two ends of the second conductor layer being electrically connected to one another, and
   a fault part formed in the first conductor layer so as to electrically disconnect the two ends of the first conductor layer when a sample to be measured is absent from the fault part.

10. The electrical measuring device according to claim 9, comprising a plurality of high-frequency transmission lines.

11. The electrical measuring device according to claim 10, wherein the plurality of high-frequency transmission lines are arranged in parallel with each other.

12. The electrical measuring device according to claim 10, further comprising a flow path for sample introduction which passes a plurality of fault parts.

13. The electrical measuring device according to claim 9, further comprising a flow path for sample introduction having the fault part as a part of the flow path.

* * * * *